United States Patent [19]

Bljumberg et al.

[11] 4,256,650

[45] Mar. 17, 1981

[54] PROCESS FOR PREPARING PROPYLENE OXIDE AND ACETIC ACID

[76] Inventors: Erna A. Bljumberg, Leninsky prospekt, 57, kv. 10; Sergei A. Maslov, Veshnyakovskaya ulitsa, 6, korpus 4, kv. 56; Nikolai M. Emanuel, Vorobievskoe shosse, 2b, kv. 44, all of Moscow; Alexandr G. Merzhanov, Noginsky raion, poselok Chernogolovka, ulitsa Pervaya, 1, kv. 30; Inna P. Borovinskaya, Noginsky raion, poselok Chernogolovka, ulitsa Pervaya, 17/1, kv. 9, both of Moskovskaya oblast, all of U.S.S.R.

[21] Appl. No.: 46,807

[22] Filed: Jun. 8, 1979

Related U.S. Application Data

[63] Continuation of Ser. No. 884,644, Mar. 8, 1978, abandoned.

[51] Int. Cl.$^3$ ............................................. C07D 301/06
[52] U.S. Cl. ................................................. 260/348.33
[58] Field of Search ..................................... 260/348.33

[56] References Cited

U.S. PATENT DOCUMENTS

| | | | |
|---|---|---|---|
| 3,699,133 | 10/1972 | Messina et al. | 260/348.33 |
| 3,716,562 | 2/1973 | Pregaglia et al. | 260/348.33 |
| 3,821,259 | 6/1974 | Bljumberg et al. | 260/348.33 |
| 3,957,690 | 5/1976 | Bobolev et al. | 260/348.33 |
| 3,993,672 | 11/1976 | Arzoumanian et al. | 260/348.33 |
| 4,077,986 | 3/1978 | Gipson | 260/348.29 |

FOREIGN PATENT DOCUMENTS 285917  11/1970  U.S.S.R. ............................. 260/348.33

*Primary Examiner*—Norma S. Milestone
*Attorney, Agent, or Firm*—Burgess, Ryan and Wayne

[57] ABSTRACT

A process for preparing propylene oxide and acetic acid which comprises oxidation of propylene and acetaldehyde with an oxygen-containing gas in a liquid phase at a temperature of from 70° to 100° C. under a pressure of from 40 to 50 atm in the presence of a catalyst, viz. a boron compound of the formula BE, wherein E is a metal of IV,V,VI Groups of the periodic system, and nitrogen. The process according to the present invention makes it possible to increase selectivity of the formation of propylene oxide as calculated from the reacted acetaldehyde.

7 Claims, No Drawings

PROCESS FOR PREPARING PROPYLENE OXIDE AND ACETIC ACID

This is a continuation, of application Ser. No. 884,644, filed Mar. 8, 1978 now abandoned.

FIELD OF THE INVENTION

The present invention relates to a process for preparing propylene oxide and acetic acid which are useful in chemical, light industries, food production, as starting material for the manufacture of polymeric, synthetic fibres and solvents.

BACKGROUND OF THE INVENTION

Known in the art is a process for preparing propylene oxide and acetic acid the oxidation of propylene and acetaldehyde with an oxygen-containing gas in a liquid phase in the presence of a homogeneous catalyst at a temperature within the range of from 150 to 250° C. As the homogeneous catalyst, use is made of salts of cobalt, manganese, ruthenium. Selectivity of the formation of propylene oxide as calculated for the reacted acetaldehyde is 35 molar percent.

This prior art process has a disadvantage because of a low selectivity of the formation of propylene oxide as calculated for the reacted acetaldehyde.

Known in the art is also a process for preparing propylene oxide and acetic acid the oxidation of propylene and acetaldehyde with an oxygen-containing gas in the presence of a heterogeneous catalyst such as silver oxide at a temperature of from 70 to 150° C. under a pressure of from 2 to 60 atm. Selectivity of the formation of propylene oxide as calculated for the reacted acetaldehyde does not exceed 70 molar percent (cf. USSR Inventor's Certificate No. 334825). This prior art process is objectionable because there is an insufficient selectivity of the formation of propylene oxide as calculated for the reacted acetaldehyde.

OBJECT OF THE INVENTION

It is an object of the present invention to increase the selectivity of the formation of propylene oxide as calculated for the reacted acetaldehyde.

BRIEF SUMMARY OF THE INVENTION

This object is accomplished by a process for preparing propylene oxide and acetic acid by subjecting propylene and acetaldehyde to oxidation with an oxygen-containing gas in a liquid phase at a temperature within the range of from 70 to 100° C. under a pressure of from 40 to 50 atm. Boron compounds of the formula BE, wherein E is a metal selected from Group IV, V and VI of the periodic system and nitrogen are catalysts for the process of the present invention. In accordance with the present invention, the catalyst used is a boride of tantalum, molybdenum, zirconium or nitrogen. It is advisable to use the catalyst in the process according to the present invention in an amount of from 0.1 to 0.2% by weight of the reaction mixture.

DETAILED DESCRIPTION OF THE INVENTION

The process for preparing propylene oxide and acetic acid in accordance with the present invention is performed in the following manner.

Into a metallic reactor there are charged the liquified starting components and a powder-like catalyst is introduced i.e., a boride of tantalum, molybdenum, zirconium or nitrogen in an amount within the range of from 0.1 to 0.2% by weight of the reaction mixture; the pressure is increased to 40-50 atm and the temperature is maintained within the range of from 70 to 100° C., whereafter the oxygen-containing gas having an oxygen content of from 10 to 100% by volume, is passed into the reaction mixture at a rate of from 10 to 12 l/hr. The reaction is conducted for 1-1.5 hours. On completion of the reaction, the desired products are separated by rectification. It is preferable to use, as the oxidizing gas, air and perform the reaction at a temperature of from 70° to 80° C. under the pressure of 40 atm. The catalyst is produced in a conventional manner as by way of a high temperature synthesis from the appropriate elements.

The use of a boride of tantalum, molybdenum, zirconium or nitrogen as the catalyst in the process according to the present invention makes it possible to increase the selectivity of the formation of propylene oxide up to 93 molar percent as calculated for the reacted acetaldehyde.

For a better understanding of the present invention the following Examples are given hereinbelow by way of illustration.

EXAMPLE 1

Into a 200 $cm^3$ metallic reactor there are charged 40 ml (24 g) of liquified propylene, 10 ml (7.5 g) of acetaldehyde and 40 ml (35 g) of benzene (solvent) and 0.1 g of tantalum boride is added thereto. The reactor is sealed, air is supplied thereinto at a pressure of 40 atm and the temperature is elevated to 70° C. Thereafter, air is bubbled through the reactor at the rate of 10–12 l/hr. After 1.25 hours the oxidation is discontinued, the pressure is released and the unreacted propylene is evaporated at room temperature.

From the remaining liquid portion, i.e., the oxidized portion, propylene oxide and acetic acid are recovered by rectification. The distillation residue is subjected to analysis.

Given hereinbelow are data identifying the contents of the oxidized composition and the yields of propylene oxide and acetic acid.

| | |
|---|---|
| Propylene oxide in the oxidized composition | 4.6 g |
| Acetic acid in the oxidized composition | 5.0 g |
| Acetaldehyde in the oxidized composition | 4.0 g |
| Conversion degree for the acetaldehyde | 49% |
| Conversion degree for the propylene | 13.8% |
| Selectivity of the formation of propylene oxide as for acetaldehyde | 93 mol.% |
| Selectvity of the formation of acetic acid as for acetaldehyde | 96 mol.% |

EXAMPLE 2

The procedure for the preparation of propylene oxide and acetic acid is carried out in accordance with the procedure in the foregoing Example 1.

As the catalyst, use is made of nitrogen boride. The oxidized composition and the yields of propylene oxide and acetic acid are given hereinbelow.

| | |
|---|---|
| Content of propylene oxide in the oxidized composition | 4.5 g |
| Content of acetic acid in the oxidized composition | 4.9 g |
| Content of acetaldehyde in the oxidized composition | 4.2 g |
| Conversion degree for the acetaldehyde | 46% |
| Conversion degree for the propylene | 13.5% |

| | |
|---|---|
| Selectvity of the formation of propylene oxide as calculated for acetaldehyde | 93% |
| Selectivity of the formation of acetic acid as calculated for acetaldehyde | 98% |

EXAMPLE 3

The procedure for the preparation of propylene oxide and acetic acide is conducted in a manner similar to that described in Example 1 hereinbefore.

As the catalyst, molybdenum boride is used and the oxidation reaction is conducted for 1.5 hours.

The oxidized composition and the yields of propylene oxide and acetic acid are given hereinbelow.

| | |
|---|---|
| Content of propylene oxide in the oxidized composition | 3.2 g |
| Content of acetic acid in the oxidized composition | 4.2 g |
| Content of acetaldehyde in the oxidized composition | 4.8 g |
| Conversion degree for the acetaldehyde | 38% |
| Conversion degree for the propylene | 8.7% |
| Selectivity of the formation of propylene oxide as calculated for acetaldehyde | 80 mol.% |
| Selectivity of the formation of acetic acid as calculated for acetaldehyde | 95 mol.% |

EXAMPLE 4

The procedure for the preparation of propylene oxide and acetic acid is conducted in a manner similar to that described in the foregoing Example 1.

As the catalyst zirconium boride is used and the oxidation reaction is carried out over a 1.5 hour.

The oxidized composition and the yields of propylene oxide and acetic acid are given hereinbelow.

| | |
|---|---|
| Content of propylene oxide in the oxidate | 3.6 g |
| Content of acetic acid in the oxidized compostion | 4.7 g |
| Content of acetaldehyde in the oxdized composition | 4.1 g |
| Conversion degree for the acetaldehyde | 47% |
| Conversion degree for the propylene | 10.9% |
| Selectivity of the formation of propylene oxide as calculated for acetaldehyde | 78 mol.% |
| Selectivity of the formation of acetic acid as calculated for acetaldehyde | 95 mol.% |

EXAMPLE 5

Into a 200 cm$^3$ metallic reactor there are charged 40 ml (24 g) of liquified propylene, 10 ml (7.5 g) of acetaldehyde and 40 ml (35 g) of benzene (solvent) and 0.2 g of tantalum boride is introduced into the reactor. The apparatus is sealed, air is passed thereinto at a pressure of 50 atm and heated to the temperature of 100° C. Thereafter, air is bubbled through the reactor at a rate of from 10 to 12 l/hr After one hour the oxidation is discontinued, the pressure is released and the unreacted propylene is evaporated at room temperature.

From the remaining liquid portion (oxidized composition) propylene oxide and acetic acid are recovered by rectification. The remaining liquid portion (oxidized composition) is subjected to analysis The data identifying the contents of the oxidized composition and the yields of propylene oxide and acetic acid are given hereinbelow.

| | |
|---|---|
| Content of propylene oxide in the oxidized composition | 4.7 g |
| Content of acetic acid in the oxidized composition | 5.1 g |
| Conversion degree for the acetaldehyde | 50% |
| Conversion degree for the propylene | 14.0% |
| Selectivity of the formation of propylene oxide as calculated for acetaldehyde | 75 mol.% |
| Selectvity of the formation of acetic acid as calculated for acetaldehyde | 92 mol.% |

What is claimed is:

1. A process for preparing propylene oxide and acetic acid comprising oxidizing propylene and acetaldehyde in the presence of an oxygen-containing gas in a liquid phase at a temperature within the range of from 70 to 100° C. under a pressure of from 40 to 50 atm in the presence of a boron compound catalyst of the formula BE selected from the group consisting of NB, TaB and MoB wherein E is tantalum, molybdenum or nitrogen.

2. A process as claimed in claim 1, wherein the catalyst is employed in an amount of from 0.1 to 0.2% by weight of the reaction mixture.

3. A process as claimed in claim 1, wherein as the catalyst tantalum boride is used.

4. A process as claimed in claim 1, wherein as the catalyst molybdenum boride is used.

5. A process as claimed in claim 1 wherein the oxidation is conducted at a temperature of 70° to 80° C. at a pressure of 40 atm.

6. A process according to claim 1 wherein the oxidation reaction is conducted for a period between 1 and 1.5 hours.

7. A process according to claim 1 wherein nitrogen boride is employed as the catalyst.

* * * * *

UNITED STATES PATENT OFFICE
CERTIFICATE OF CORRECTION

Patent No. 4,256,650          Dated March 17, 1981

Inventor(s) Erna A. Bljumberg, et al

It is certified that error appears in the above-identified patent and that said Letters Patent are hereby corrected as shown below:

In the Abstract, line 10: "from" should be --for--.

Column 3, line 22: "8.7%" should be --9.7%--.

line 33: After "hour" insert --period--.

line 37: "oxidate" should be --oxidized composition--.

Signed and Sealed this

First Day of September 1981

[SEAL]

Attest:

Attesting Officer

GERALD J. MOSSINGHOFF
Commissioner of Patents and Trademarks

UNITED STATES PATENT OFFICE
CERTIFICATE OF CORRECTION

Patent No. 4,256,650     Dated August 19th, 1981

Inventor(s) Erna A. Bljumberg, et al

It is certified that error appears in the above-identified patent and that said Letters Patent are hereby corrected as shown below:

Column 3, line 10: "acide" should be -- acid --.

line 33: After "hour" insert -- period --.

line 37: "oxidate" should be -- oxidized composition --.

Signed and Sealed this

Twenty-seventh Day of October 1981

[SEAL]

Attest:

Attesting Officer

GERALD J. MOSSINGHOFF

Commissioner of Patents and Trademarks